(12) United States Patent
Silver

(10) Patent No.: US 8,353,926 B2
(45) Date of Patent: Jan. 15, 2013

(54) LONG-TERM RETRIEVABLE MEDICAL FILTER

(75) Inventor: James H. Silver, Palo Alto, CA (US)

(73) Assignee: Cordis Corporation, Miami Lakes, FL (US)

( * ) Notice: Subject to any disclaimer, the term of this patent is extended or adjusted under 35 U.S.C. 154(b) by 851 days.

(21) Appl. No.: 10/592,910

(22) PCT Filed: Apr. 15, 2005

(86) PCT No.: PCT/US2005/013039
§ 371 (c)(1),
(2), (4) Date: May 14, 2007

(87) PCT Pub. No.: WO2005/102439
PCT Pub. Date: Nov. 3, 2005

(65) Prior Publication Data
US 2008/0033479 A1 Feb. 7, 2008

Related U.S. Application Data

(60) Provisional application No. 60/562,456, filed on Apr. 15, 2004.

(51) Int. Cl.
*A61M 29/00* (2006.01)
(52) U.S. Cl. ............................................... 606/200
(58) Field of Classification Search ............ 606/200, 606/108, 114, 127; 623/1.11; 128/831, 843
See application file for complete search history.

(56) References Cited

U.S. PATENT DOCUMENTS

| 5,234,458 | A | 8/1993 | Metais | |
|---|---|---|---|---|
| 6,099,549 | A | 8/2000 | Bosma et al. | |
| 6,241,746 | B1 | 6/2001 | Bosma et al. | |
| 6,267,777 | B1* | 7/2001 | Bosma et al. | 606/200 |
| 6,315,708 | B1* | 11/2001 | Salmon et al. | 600/3 |
| 6,364,895 | B1 | 4/2002 | Greenhalgh | |
| 6,443,972 | B1 | 9/2002 | Bosma et al. | |

(Continued)

FOREIGN PATENT DOCUMENTS

DE 4030998 A1 4/1991

(Continued)

OTHER PUBLICATIONS

European Search Report dated Nov. 20, 2008 for corresponding Appln No. EP 05734557.

*Primary Examiner* — Gary Jackson
*Assistant Examiner* — Jonathan Hollm

(57) ABSTRACT

A medical filter has more than one pair of struts extending along an undulating path between a first and second end, which cooperate to define a first and second filter element having a plurality of cells, connected by a central portion with longitudinal strut sections. The struts extend between the first and second ends, and the struts tend to resiliently expand in radially outward directions from a compressed initial shape to an expanded deployed shape. In the expanded shape, the undulating path is defined by (i) a first portion of each pair of ribs extends substantially adjacent to each other for a distance from the first end, (ii) a second portion of each pair of ribs extends substantially adjacent to each other for a distance from the second end; and (iii) an intermediate portion of each one of a pair of ribs extends to curve away from each other.

5 Claims, 3 Drawing Sheets

U.S. PATENT DOCUMENTS

| | | |
|---|---|---|
| 6,540,722 B1 | 4/2003 | Boyle et al. |
| 6,989,021 B2 | 1/2006 | Bosma et al. |
| 7,044,134 B2 | 5/2006 | Khairkhahan et al. |
| 2001/0025187 A1 | 9/2001 | Okada |
| 2003/0023265 A1* | 1/2003 | Forber ......................... 606/200 |
| 2003/0120303 A1* | 6/2003 | Boyle et al. .................. 606/200 |
| 2003/0130680 A1* | 7/2003 | Russell ........................ 606/200 |
| 2005/0165441 A1* | 7/2005 | McGuckin et al. ........... 606/200 |

FOREIGN PATENT DOCUMENTS

| | | |
|---|---|---|
| DE | 19509464 C1 | 6/1996 |
| FR | 2718950 A1 | 10/1995 |

* cited by examiner

LONG-TERM RETRIEVABLE MEDICAL FILTER

CROSS-REFERENCE TO RELATED APPLICATION

This application claims the benefit of priority of U.S. Provisional Patent Application No. 60/562,456 filed on Apr. 15, 2004.

BACKGROUND AND SUMMARY OF THE INVENTION

1. Technical Background

The present invention relates to medical devices, and more particularly to a retrievable medical filter.

2. Discussion

Some basic types of vascular filters are generally known, wherein a single filter element, mesh or member extends across the direction of flow inside a blood vessel. Several features may be desirable for vascular filters, including non-surgical or "percutaneous" delivery of the filter to a desired site, and expansion from a preferably small initial size to an expanded working size that matches the vascular anatomy at the desired site. Also, a vascular filter should preferably capture a sufficient percentage of thrombus, while allowing blood to flow freely through the filter.

Another desirable feature is a capability to remain reliably in the desired position in a patient's anatomy, referred to as "position retention." One simple attempt at position retention is to wedge a vascular filter against the blood vessel wall by sizing it with a dimension slightly larger than the inside diameter of the blood vessel. In addition, a vascular filter should preferably have a design whereby the filter is self-centering and stable in the vessel, such that the filter has a tendency not to "tilt", which might result in less effective capturing of thrombus. Some vascular filters may be used in the vena cava, and may be described in such event as a "vena cava filter."

A vascular filter may be delivered through a catheter in a compressed shape, the filter tending to resiliently expand within a blood vessel and to retain the desired position and orientation. The vascular filter tends to trap thrombus or particles, and resist their movement further downstream. The filter includes, in a position of use, an outer shape corresponding to the internal diameter of the blood vessel, and one or more filter elements extending across the vessel.

In the temporal sense, there are three types of filters: (i) permanent filters, intended for permanent implantation; (ii) temporary filters, intended for removal within a time period; and (iii) retrievable filters, in which the physician has the option to implant the filter permanently or to remove the filter after some time. In the case of a retrievable filter, the filter may be designed so that the physician can choose whether to retrieve the filter at a later date, after the filter has been in place for a while. This way, the physician can evaluate the performance of the filter and the patient's condition, before deciding whether to retrieve the filter or not.

Regarding retrieval, one factor is "endothelialization" or in-growth of the vessel wall and tissue around the structural members of the filter. In other words, endothelialization is the healing of the vessel inner surface by endothelial cells, and it is desirable to preserve these endothelial cells when removing a retrievable vascular filter. The improved designs of the present invention tend to minimize any impact during retrieval.

Prior vascular filters have a demonstrated track record of filtering clots due to their filter basket design. However, because of the tendency of neointimal tissue to grow over the struts and other filter elements, may cause the filter to become mechanically interlocked with the tissue. When the tissue develops sufficient strength, the filter may no longer be retrievable. For some prior retrievable filters, this may occur somewhere between two and three weeks following implantation.

There are several connection points where a filter may become interlocked with tissue, depending on the size of the vena cava or other body passage in which the device is placed. These include parallel struts between front and back filter baskets, at a shoulder or the filter basket, and at a diamond bifurcation.

According to the principles of the present invention, in order to retain the clot capturing capabilities of the filter baskets, these new filter baskets may be formed by laser-cutting a series of straight, parallel struts, and then shape-setting them in a way so that they closely resemble the filter baskets. As illustrated in the drawings, by forming the baskets from straight, parallel struts, all connections between struts are removed, so that the filter tends not to become interlocked with tissue.

The filter therefore may be retrievable for a longer time or possibly an indefinite period. It may also be desirable to have a filter which consists of two of these filter baskets, one caudal and one cranial, in order to prevent the filter from tilting. Further, in order to facilitate retrievability, it may also be desirable to connect both filter baskets in the middle, and for both filters to be sloped in the same manner as the caudal basket of the filter. In this manner, the outer legs of the filter can act as anchors to prevent migration of the filter.

This filter design provides the demonstrated clot capturing ability of the filter, but the filter elements are shaped from unconnected, straight parallel struts, which allow the filter to be removed from the tissue at a selected time without a tendency for affecting the vessel wall. This is because these struts are not physically connected to each other, and can separate during retrieval.

In addition, this type of filter is compatible with a bi-directional retrieval system. As shown in FIGS. 4 and 5, because the filter struts are not physically attached to each other, as is the case with prior filters, the catheter can be inserted through the windows of the flower basket, without risking entanglement of the catheter. If the retrieval catheter is inserted through one of the windows of the flower basket, the window of the flower basket can be opened, as shown in FIG. 3, to allow the retrieval catheter to slip through.

It is also possible to change the filter basket by adding or subtracting even numbers of struts, so that the number of windows within the flower basket changes from six to five, seven, or some other number. It is also possible to change the direction that the flow baskets face. That is, the cranial basket can be oriented in the same direction as the cranial basket on another filter.

A vascular filter along the lines of the present invention may provide several advantages, including effectively capturing thrombus while allowing blood flow, and resisting endothelialization of the filter. In other words, the filter enables a physician to have a longer time before choosing whether to retrieve a retrievable filter.

A vascular filter may have an initial compressed shape, in which the filter may have essentially a tubular shape, and may be contained in a lumen or passage defined by a catheter.

After a distal tip of the catheter reaches a desired site for treatment, a wire mandrel or other deployment device may be used to push the filter out of the catheter. And when the filter is released from the catheter, it tends to resiliently expand from the initial compressed shape to an expanded shape. When a vascular filter is retrieved from a blood vessel, the entire filter is resiliently compressed to a relatively small diameter, for extraction through a catheter.

The term "filter" will be used interchangeably, to refer to either (i) a combination device including a resilient scaffold structure with a sleeve covering, or (ii) those portion(s) of the scaffold which operate to capture thrombus.

The term "tubular" is used in its broadest sense, to encompass any structure arranged a radial distance around a longitudinal axis. Accordingly, "tubular" includes any structure that (i) is cylindrical or not, such as for example an elliptical or polygonal cross-section, or any other regular or irregular cross-section; (ii) has a different or changing cross-section along its length; (iii) is arranged around a straight, curving, bent or discontinuous longitudinal axis; (iv) has an imperforate surface, or a periodic or other perforate, irregular or gapped surface or cross-section; (v) is spaced uniformly or irregularly, including being spaced varying radial distances from the longitudinal axis; (vi) has any desired combination of length or cross-sectional size.

A vascular filter may include a first and second filter section, arranged on either side of a body section. The body section and the filter sections thus enclose a space. Due to the elongated shape of the vascular filter, and the arranging of the first and second filter sections on either side of the body member, the present filter may have an enhanced filtering effect. In other words, two opportunities have been created for intercepting thrombus moving inside the blood vessel.

A central tubular section tends to resiliently exert slight outward pressure along a large section of contact area on the blood vessel wall. The sleeve distributes this outward pressure to a greater area. Accordingly, the filter tends to exert some small amount of pressure on the internal wall of the blood vessel, and tends to hold itself in place. The vascular filter will consequently tend not to shift position. In addition, because of this elongated shape the vascular filter tends to center itself within the lumen, and not to rotate transversely or tilt over.

In an example, a vascular filter may be formed out of one single piece, which provides advantages including simplicity.

When viewed along the longitudinal axis of the filter, the filter sections may have the shape of a regular polygon, and thus may provide several smaller filtering "cells". The purpose of these filtering cells is to intercept thrombus moving inside the blood vessel, and the smaller filtering cells tend to capture more thrombus. All the cells may be of the same size, to provide a uniform filtering effect.

The filter sections, as arranged according to an embodiment described above on either side of the tubular body section, may be identical in shape, thereby enhancing the simplicity of the vascular filter according to the present invention.

It is of course possible to build various vascular filters according to the present invention, by various techniques and of various materials to obtain the desired features. It should be noted that the present invention also relates to methods for manufacturing vascular filters, and for using vascular filters for medical treatment of a patient.

These and various other objects, advantages and features of the invention will become apparent from the following description and claims, when considered in conjunction with the appended drawings. The invention will be explained in greater detail below with reference to the attached drawings of a number of examples of embodiments of the present invention.

DETAILED DESCRIPTION OF THE PREFERRED EMBODIMENTS

The following description of the preferred embodiments of the present invention is merely illustrative in nature, and as such it does not limit in any way the present invention, its application, or uses. Numerous modifications may be made by those skilled in the art without departing from the true spirit and scope of the invention.

The drawings depict a vascular medical filter 10 along the lines of the present invention.

Filter 10 has an expanded shape, and an initial compressed shape. If filter 10 is delivered with a catheter and a pushing wire or mandrel, filter 10 will have the initial compressed shape when it is within a passage or lumen of the catheter. In this configuration, the filter may have a tubular shape, and a pattern of struts or ribs may be affixed together or be made of a single piece of material with a series of cuts.

In any event, filter 10 tends to resiliently expand from the initial compressed shape to the expanded shape. Once the filter 10 is in the expanded shape, it tends to resiliently maintain that expanded shape, when deployed at a desired site for treatment within a body passage or vessel.

Filters of the present invention may be made with various manufacturing methods, including providing an initial tube, and then cutting a series of struts in the tube to enable expansion into the desired shape. Various other methods are of course possible, including forming the filter of discrete members and joining or connecting the members, or chemically etching a substrate. The manufacturing methods may include an inflatable or expandable mold, heating or cooling, welding, etc.

Figure 3:
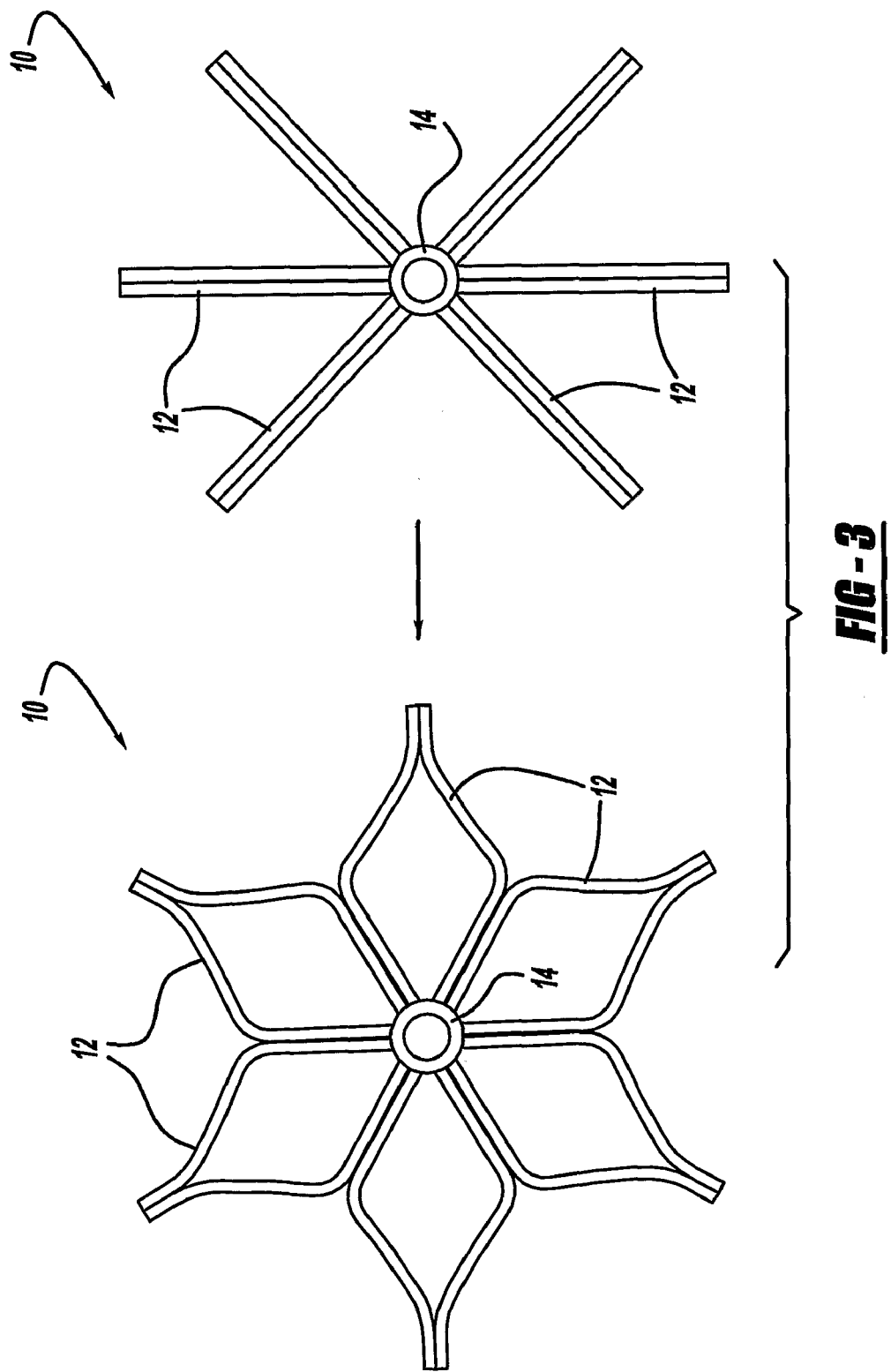
FIG. 3 is a diagrammatic end elevation view of a medical filter showing two stages in a process for making a medical filter.

To clarify one possible method of making a filter, an initial tubular form defines a longitudinal axis and has first and second ends 14 and 16. More than one pair of struts 12 are cut in the tubular form, so as to define struts 12 extending between the first and second end 14 and 16; and the struts are treated so that they tend to resiliently expand from a compressed shape to an expanded shape. As shown in FIG. 3, a central portion of each of the struts 12 is expanded in a radially outward direction, such that a gap is defined between the pairs of struts 12, and the individual struts 12 of each pair follow a path which is substantially adjacent to the other strut 12 of that pair. In the drawings, six pairs of struts are shown, but of course any suitable number of strut pairs may be selected.

Next, a central portion of each of the struts is bent to follow an undulating path in the expanded shape, as shown in the second diagram of FIG. 3 which is indicated by the arrow. Accordingly, in the expanded shape a first portion of each pair of ribs extends substantially adjacent to each other for a distance from the first end, and a second portion of each pair of ribs extends substantially adjacent to each other for a distance from the second end; wherein an intermediate portion of each one of a pair of ribs is bent to curve away from each other in the expanded shape.

Figure 2:
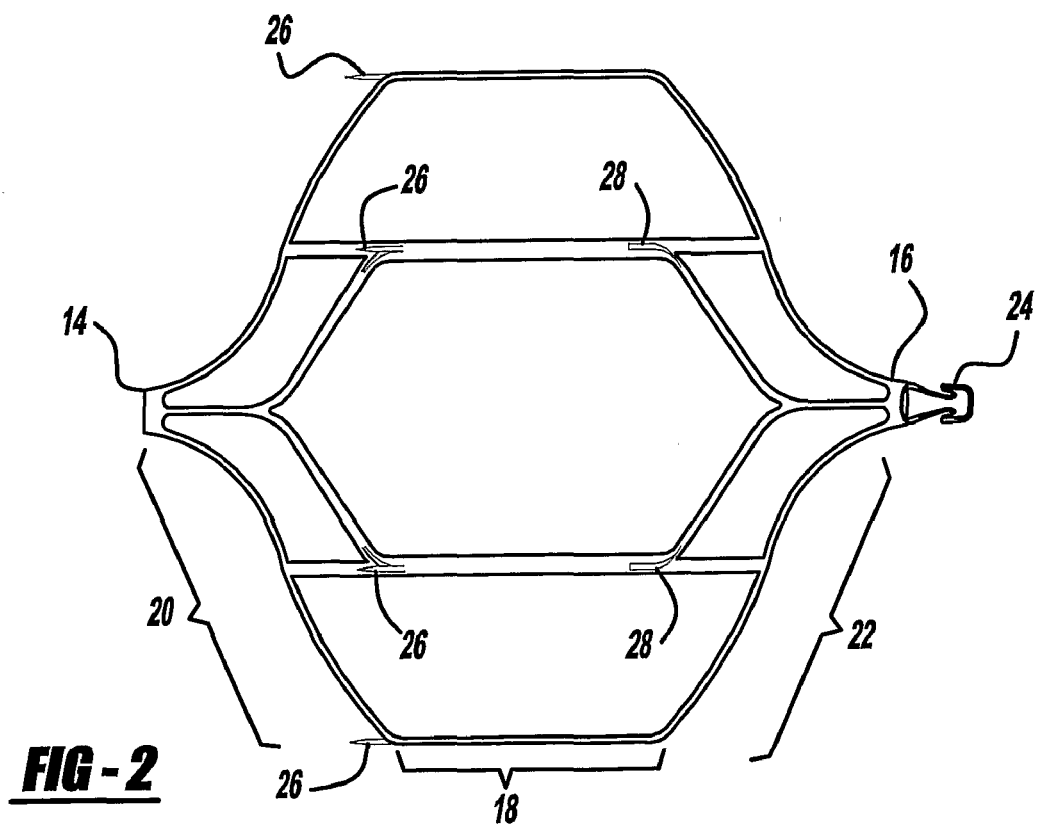
FIG. 2 shows a side elevation view of a vascular filter.

Structurally, when viewed from the side in FIG. 2, the filter in the expanded deployed shape has a central section 18, flanked by a first and second filtering section 20 and 22, which are flanked by the first and second end 14 and 16. The particular example depicted in the drawings is made from a single piece of tubular material, with a patterned series of cuts, which is treated to resiliently expand and form the filtering mesh structure. The filter structure could of course also be formed of multiple members which are affixed together.

The terms "filter" or "vascular filter" or "filtering" may be used in a broad or interchangeable fashion to refer generally to the entire filter 10, the first and second filtering section 22 and 24, the filtering effect on body fluids or particulates, or the results of such a filtering effect, or any other relevant aspect of the present invention.

While the filter 10 is implanted within a patient, body tissues naturally tend to incorporate or endothelialize implanted objects. This process of endothelialization may take place over a predictable period of time, and when a filter or other medical device has been incorporated or endothelialized, it may be preferred to leave it in place indefinitely. The "disconnected parallel structure" of the struts of the filter may tend to extend this period of time of incorporation, allowing medical filter to remain in place and provide therapeutic benefit for a longer period of time, yet continue to be retrievable.

Figure 4:
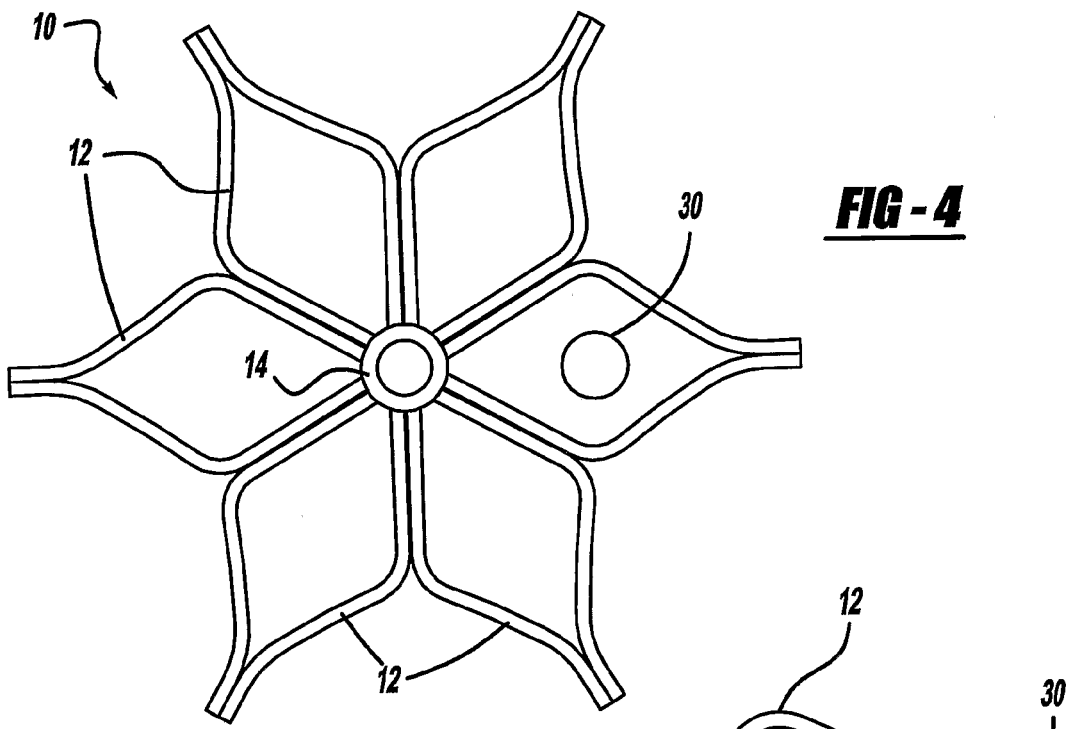
FIG. 4 shows an end elevation view of a vascular filter and another device, such as a catheter or guidewire.
Figure 5:
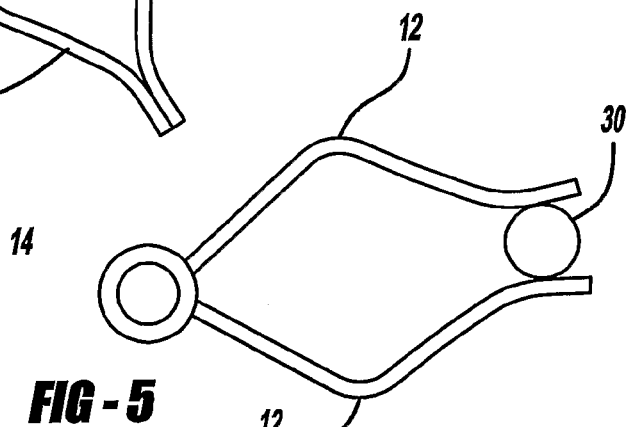
FIG. 5 shows a partial end elevation view of a vascular filter and another device, such as a catheter or guidewire.

Likewise, the parallel structure of the struts not only reduces trauma to the vessel during removal, it also facilitates removal of the filter using a catheter to pull the filter into a lumen defined by the catheter, by pulling the filter in distal direction, rather than the proximal direction. As illustrated in FIGS. 4 and 5, a catheter is often used to retrieve implanted filters, but it may be desirable to approach the filter from a direction opposite to the direction the filter may be optimally retrieved. With the filters of the present invention, the catheter 30 may be inserted through the cells of the filter itself, yet without interfering with those cells. Referring to FIG. 5, the struts 12 of the filter will tend to resiliently expand, allowing the catheter 30 to escape the cell of the filter in a radial direction.

If the filter is intended to be a temporary or a retrievable filter, such that the filter may be removed or retrieved at a later time, the filter may be provided with features advantageous to such possible retrieval. For example, the filter 10 shown in FIG. 2 has some additional optional features, that may be included but are not required in a filter arranged according to the present invention, including a hook structure 24, barbs or anchors 26, and apertures 28. Barbs 26 may be desirable to provide releasable temporary position stabilizers, to resist tilting and to enhance position retention. Hook 24 may be used to extract the filter 10 back into a catheter by means of a cooperating hook, snare or grabbing member.

In the compressed shape when the vascular filter is inside the catheter, the filter may include cuts extending in the longitudinal direction of the filter between, but not as far as, the ends of the filter. The cuts define strips of material as illustrated in the drawings. These strips expand to form the filtering first and second mesh, and the ribs. The specific cuts consequently also form the filter elements 20 and 22 on either side of the filter 10. The strips extend in a generally longitudinal direction in the compressed shape.

The vascular filter embodiment illustrated here may of course be used in the vena cava or any other desired site for treatment. The filter includes a number of ribs or struts extending in a generally undulating longitudinal direction. Liquid inside the blood vessel can pass through the vascular filter, but thrombus or particulates tend to be intercepted by one of the two filter sections 20 or 22.

As the filter sections 22 and 24 have been arranged on either side of the central body of the filter, a longitudinally symmetrical shape may be obtained (except for hook 24). In such a configuration, there is no difference whether the vascular filter is placed forward or backward inside the blood vessel. In other words, the proximal and distal ends of the filter may be identical and symmetrical. Accordingly, a single pre-loaded catheter system may be used to deploy a filter at a desired site, from either an upstream or downstream direction.

Figure 1:
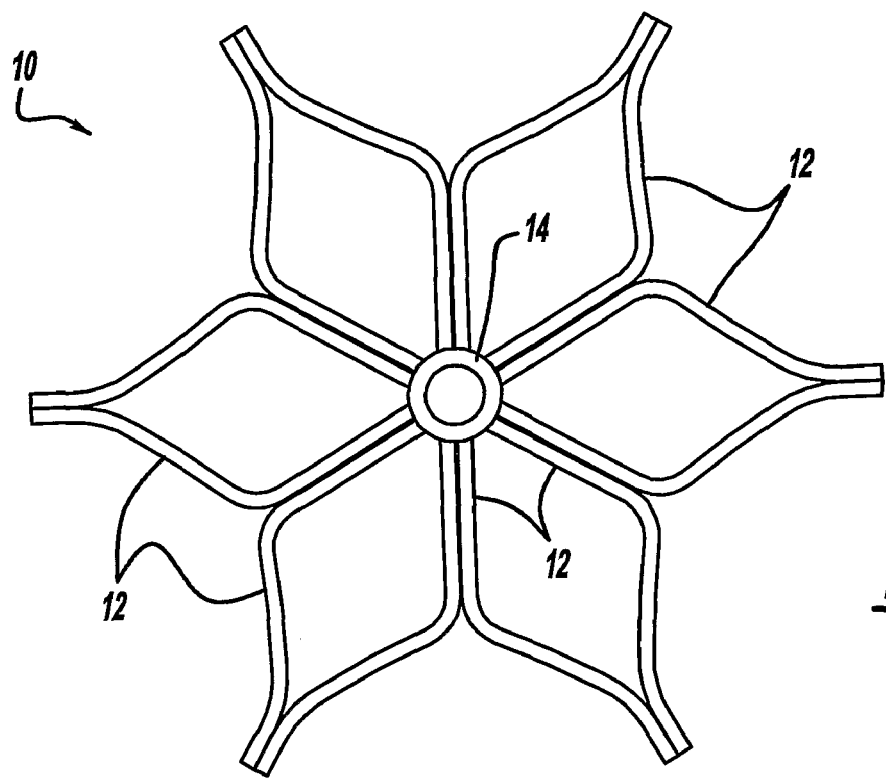
FIG. 1 illustrates an end elevation view of the vascular filter.

In the axial view of FIG. 1, the filter sections on either side of the ribs of the vascular filters according to the present invention described above display diamond or polygon shapes. It is also possible to provide vascular filters of which the filter sections display in axial view a star shape, or any other suitable shape, as long as they successfully intercept blood clots or thrombus. An advantage of this feature is that, after passing the first filter section and the tubular section or the elongated body member, a second filter element for intercepting thrombus has been provided. Also, other shapes of the filter sections in axial view are possible, which shapes will occur to those skilled in the field after reading the present description. The shapes of the filter sections in axial view need not be symmetrical, and may in principle have any suitable appearance.

The filter may for example be delivered to the vascular region in the general area of the heart from either a femoral artery access point in the leg, or a jugular artery access point in the neck. Because the filter shown in FIG. 2 may be longitudinally symmetrical, the same filter delivery system may be used for either femoral or jugular access.

Furthermore, retraction of a vascular filter according to the present invention is mentioned above, which should not limit the scope of the claims attached. Regarding the subject of the invention, it is therefore of no consequence whether the filter is placed permanently, in a removable manner, temporarily or otherwise.

Vascular filters according to the present invention may be made of any suitable material using a variety of methods. One material having the desired characteristics of strength, resilience, flexibility, biocompatibility and endurance is nitinol. Other possible materials include stainless steel and any other material having the desired properties.

Figure 6:
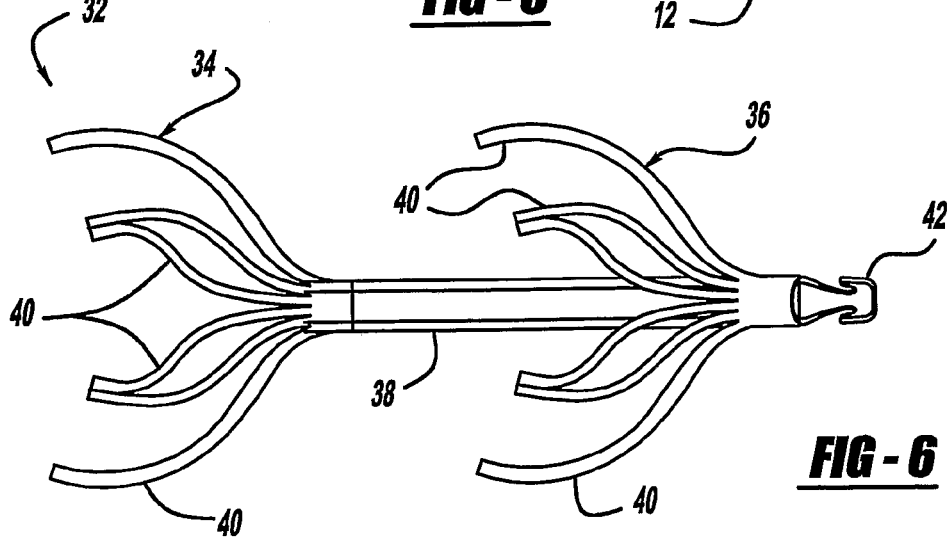
FIG. 6 shows a side elevation view of a medical filter.

A possible alternate embodiment of the present invention is depicted in FIG. 6, in which a filter 32 has a first and second filter section 34 and 36, connected by a central shaft 38. The filter elements 34 and 36 are formed of individual struts 40, which follow a curving path to define filtering cells with outermost point that are not connected. This "disconnected" structure, similar to that of the filter 10 in FIGS. 1-5, allows tissues (and/or other medical devices) to pass outward without binding. A hook 42 may be provided for facilitating retrieval of the filter.

It should be understood that an unlimited number of configurations for the present invention could be realized. The foregoing discussion describes merely exemplary embodiments illustrating the principles of the present invention, the scope of which is recited in the following claims. Those skilled in the art will readily recognize from the description, claims, and drawings that numerous changes and modifications can be made without departing from the spirit and scope of the invention.

What is claimed is:

1. A medical filter for therapeutic treatment of a patient, comprising:

a first and second end defining a longitudinal axis; more than one pair of ribs extending between the first and second ends, the ribs tending to resiliently expand in radially outward directions from a compressed initial shape to an expanded deployed shape; wherein in the compressed initial shape, the ribs each follow a path substantially parallel to the longitudinal axis; wherein in the expanded deployed shape, the ribs each follow an undulating path, such that a first portion of the ribs of each pair of the more than one pair of ribs extends substantially adjacent to each other in a radially outward direction for a distance from the first end, and a second portion of the ribs of each pair of the more than one pair of ribs extends substantially adjacent to each other in a radially outward direction for a distance from the second end, and an intermediate portion of each one of a pair of ribs tends to curve away from each other to touch an intermediate portion of a rib of an adjacent pair of ribs in the expanded deployed shape, wherein the touching intermediate portions of adjacent ribs are configured as a disconnected parallel structure such that the touching intermediate portions touch one another but are separable; wherein in the expanded deployed shape, the filter defines a first and second filtering portion near the first and second end, respectively with a central section therebetween, the medical filter being formed from a single thin walled tube, the medical filter being configured for long term implantation in a patient via complete separation from a delivery catheter such that the delivery catheter may be removed, the medical filter also comprising means for capture and removal via a catheter, the filter being sized for use in the vena cava.

2. The filter of claim 1, wherein in the expanded shape, a central portion of each rib tends to extend parallel to the longitudinal axis.

3. The filter of claim 1, wherein the filter has at least three pairs of ribs.

4. The filter of claim 1, wherein the filter has six pairs of ribs.

5. The filter of claim 1, wherein the filter is made of nitinol.

* * * * *